United States Patent [19]

Owen et al.

[11] 4,046,827

[45] Sept. 6, 1977

[54] HIGH SELECTIVITY TRANSALKYLATION

[75] Inventors: Hartley Owen, Belle Mead; Paul B. Venuto, Cherry Hill; Edward T. Habib, Jr., Mantua, all of N.J.

[73] Assignee: Mobil Oil Corporation, New York, N.Y.

[21] Appl. No.: 616,966

[22] Filed: Sept. 26, 1975

[51] Int. Cl.² .................................................. C07C 3/62
[52] U.S. Cl. .................................................. 260/672 T
[58] Field of Search ...................................... 260/672 T

[56] References Cited

U.S. PATENT DOCUMENTS

| | | | |
|---|---|---|---|
| 3,763,260 | 10/1973 | Pollitzer | 260/672 T |
| 3,769,360 | 10/1973 | Harper et al. | 260/672 T |
| 3,907,914 | 9/1975 | Willis et al. | 260/672 T |
| 3,926,782 | 12/1975 | Plank et al. | 260/672 T |
| 3,926,782 | 12/1975 | Plank et al. | 260/672 T |
| 3,928,172 | 12/1975 | Davis et al. | 208/120 |

*Primary Examiner*—C. Davis
*Attorney, Agent, or Firm*—Charles A. Huggett; Raymond W. Barclay; Dennis P. Santini

[57] ABSTRACT

A process is provided for high selectivity transalkylation of alkylaromatic hydrocarbon compounds of from 7 to 10 carbon atoms which comprises contacting said alkylaromatic hydrocarbon compounds with a transalkylating agent in the presence of a porous acid-active zeolite catalyst having a fluid activity index of at least about 18 in a fluidized catalyst system absent added hydrogen at a temperature of from about 300° F to about 1200° F, pressure of from about 0 psig to about 200 psig and a catalyst residence time of from about 0.01 second to about 300 seconds.

20 Claims, 1 Drawing Figure

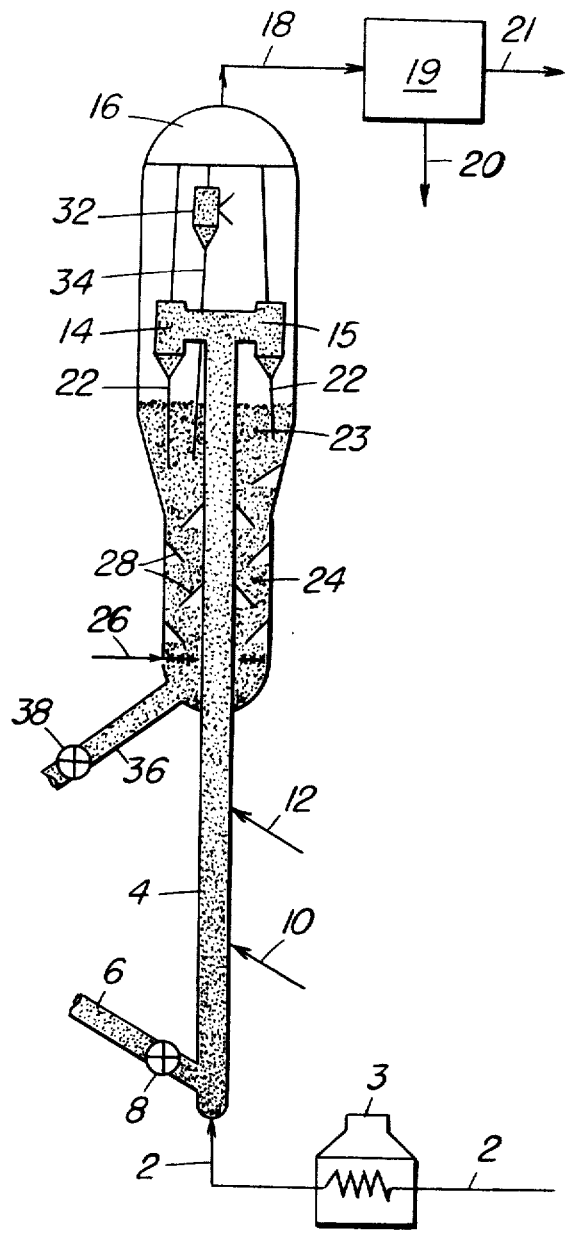

HIGH SELECTIVITY TRANSALKYLATION

BACKGROUND OF THE INVENTION

1. Field of the Invention

This invention involves a process for high selectivity, short contact time, catalytic transalkylation of alkylaromatic hydrocarbon compounds of from 7 to 10 carbon atoms, e.g. toluene, wherein the transalkylation is performed in a fluidized catalyst system absent added hydrogen. The catalyst for use in the present process is a porous acid-active zeolite having a fluid activity index of at least about 18. High selectivity to desired product, e.g. greater than equilibrium amounts of paraxylene from a feedstock of toluene, is achieved by way of the present process when reaction conditions are maintained within the following approximate ranges:

| | |
|---|---|
| Reactor inlet temperature | 300° F – 1200° F |
| Reactor pressure | 0 psig – 200 psig |
| Catalyst/alkylaromatic hydrocarbon compound feedstock (wt/wt) | 1 – 60 |
| Catalyst residence time | 0.01 second – 300 seconds |
| Feedstock residence time | 0.01 second – 300 seconds |
| Slip ratio, defined as the ratio of catalyst residence time to feedstock residence time | 1 – 2 |

2. Description of Prior Art

U.S. Pat. No. 3,551,509 discloses transalkylation between trimethylbenzenes and toluene to yield xylenes and benzene in the presence of a crystalline aluminosilicate catalyst having pore openings of 8 to 15 Angstrom units and, preferably containing Group VIII metals, hydrogen and rare earth cations. The above patent is also the subject of U.S. Pat. No. Re. 27,639.

In the area of aromatic disproportionation, Grandio et al. teach in the *Oil and Gas Journal*, Vol. 69, Number 48 (1971) a liquid-phase toluene disproportionation process utilizing zeolite catalysts in the absence of hydrogen. They further teach that vapor-phase toluene disproportionation requires hydrogen recycle or else frequent regeneration of catalyst to keep coke levels low on the catalyst and to maintain catalytic activity over any reasonable period of time.

Otani teaches in *Chemical Engineering*, 77(16), 118 (1970), that vapor-phase catalyst disproportionation of toluene requires hydrogen recycle to keep the zeolite catalyst from excessive coke build-up and, thereby, maintain reasonable catalyst activity.

U.S. Pat. Nos. 3,126,422; 3,413,374; 3,598,878; 3,598,879; and 3,607,961 show vapor-phase disproportionation of toluene over various catalysts.

Unfortunately, while many of the prior art processes proposed for transalkylation, including disporportionation, of alkylaromatic hydrocarbon compounds provide satisfactory initial yields of desired products, they do not provide the short contact time, high selectivity benefits associated with the present process. Further, no hydrogen is used in the present process, the presence of which is taught to be necessary by the prior art, thus enabling the user of the present process to realize substantial processing economies.

SUMMARY OF THE INVENTION

It has now been discovered that short contact time processing of alkylaromatic hydrocarbon compounds of from 7 to 10 carbon atoms and a suitable transalkylating agent in the absence of hydrogen over a catalyst comprised of a porous acid-active zeolite having a fluid activity index of at least about 18 in a fluidized catalyst system results in high selectivity transalkylation of said alkylaromatic hydrocarbon compounds. For example, when toluene is both the alkylaromatic hydrocarbon feedstock to the present process and the transalkylating agent, substantial conversion thereof to benzene and a highly useful mixture of xylenes occurs. In that instance, only trace quantities of ethylbenzene are formed and further transalkylation of product xylenes to form trimethylbenzenes and higher aromatics is very small. Further, in the instance where toluene is the feedstock and transalkylating agent to the present process, greater than equilibrium amounts of highly desirable paraxylene are formed. Regardless of the alkylaromatic hydrocarbon used as feedstock in the present process, the small quantity of gaseous product formed is useful as alkylation plant feed or as a chemical feed stock to other processes.

Non-limiting examples of said porous acid-active zeolites having a fluid activity index, hereinafter FAI, of at least about 18, which are useful as the catalyst for the present process include the following:

1. rare earth exchanged zeolite Y,
2. rare earth exchanged zeolite X,
3. rare earth exchanged zeolite Y combined with mordenite,
4. dealuminized mordenite,
5. hydrogen exchanged zeolite ZSM-5,
6. hydrogen exchanged zeolite ZSM-35,
7. hydrogen exchanged zeolite ZSM-38,
8. rare earth exchanged zeolite ZSM-5, and others.

The process of this invention is conducted in a fluidized catalyst system, preferably in a riser/transport system or dilute phase bed. In contrast to a fixed bed type of aromatics upgrading process, the present process allows for continuous throughput at commercially acceptable rates without loss of down time due to the need for periodic, often complicated and sensitive regeneration procedures. This is possible because of the continuous regeneration aspect of the gas-solids fluid or dilute phase process. Another beneficial consequence of continuous regeneration is that the feed molecules are presented with a clean, uncoked catalyst surface, which utilizes the maximum catalyst selectivity potential of the acidic solid. Another favorable aspect is that the present process can employ, if desired, present commercially available, thermally stable, regenerable, proved FCC cracking catalysts. Another favorable aspect is that no expensive hydrogen gas is needed in the present process.

A particular advantage of this process concept is that it operates at low pressures (i.e. at pressure commonly employed in current fluid catalytic cracking operations or slightly higher). It allows highly efficient contact of gaseous reactant with solid, high surface area acidic catalysts, with efficient mixing, uniform temperature, and rapid separation and reaction quenching. Problems due to diffusion/mass transport limitations and/or heat transfer are minimized. While this process is preferred in riser or dilute phase beds, it is also applicable in fluidized dense beds. Single or multi-stage operations can be utilized. It is particularly suited for varying conversion severity and/or product selectivity in a highly flexible manner, since catalyst and hydrocarbon residence times, catalyst/hydrocarbon ratio, temperature, and catalyst activity and type can be rapidly and smoothly varied within a short time if so desired. Further, catalyst or feedstocks can be varied rapidly, and, if desired, run in blocked out operation.

A highly flexible petrochemical processing operation built around this fluid cat cracking-type technology could develop. Such petrochemical complex could logically be interlocked with existing refinery/chemical operations.

DESCRIPTION OF THE DRAWING

The drawing depicts a typical fluidized catalyst system, e.g. a riser/transport system, for use in the present process whereby an alkylaromatic hydrocarbon feedstock may advantageously be transalkylated at short contact time to provide a product exhibiting highly selective conversion.

As shown in the drawing, an alkylaromatic hydrocarbon feedstock and transalkylating agent, as described herein, are fed via line 2 through feed preheater 3 into the inlet of riser 4 for admixture with hot catalyst introduced via standpipe 6 provided with flow control valve 8. The catalyst may be hot, regenerated catalyst from a regeneration or catalyst cascaded from a previous chemical or hydrocarbon conversion reaction, such as, for example, from a fluid catalytic cracking process. The mixture of catalyst, hydrocarbon feedstock and transalkylating agent travels up the riser 4, within which reaction takes place under reaction conditions described herein. Residence time within the herein described limits is controlled by retaining the suspension initially formed in the riser 4 during flow therethrough. Additional hydrocarbon feedstock and/or transalkylating agent may be introduced to riser 4 at one or more spaced apart downstream feed injection points 10 and 12 for residence times less then that employed for the feed introduced by line 2 but within the residence time limits herein described.

The hydrocarbon vapor-catalyst suspension passed upwardly through riser 4 is discharged into one or more cyclonic separation zones about the riser discharge and represented by cyclone separators 14 and 15. There may be a plurality of cyclone separator combinations comprising first and second cyclonic separation means attached to the riser discharge for separating catalyst particles from hydrocarbon vapors. Separated hydrocarbon vapors are passed from separators 14 and 15 to a plenum chamber 16 for withdrawal therefrom by conduit 18. Hydrocarbon vapors and gasiform material separated by stripping gas as defined below are passed by conduit 18 to separation equipment 19. From separation equipment 19 passes liquid product through line 20. Through line 21 passes gaseous product which may be useful for alkylation plant feed or as a chemical feedstock.

Catalyst separated from hydrocarbon vapors in the cyclonic separation means is passed by diplegs represented by dipleg 22 to a dense fluid bed of separated catalyst 23 retained about an upper portion of riser 4. Catalyst bed 23 maintained in a dense fluid bed condition by rising gasiform material passes downwardly through a stripping zone 24 immediately therebelow and counter-current to rising stripping gas introduced to a lower portion thereof by conduit 26. Baffles 28 are provided in the stripping zone to improve the stripping operation.

The stripping gas with desorbed hydrocarbons passes through one or more cyclonic separation means 32 wherein entrained catalyst fines are separated and returned to the catalyst bed 23 by dipleg 34. On the other hand, riser 4 may terminate with the commonly known bird cage discharge device or an open end "T" connection may be fastened thereto which is not directly connected to cyclonic separation means. The cyclonic separation means may be spaced apart from the riser discharge so that an initial catalyst separation is effected by a change in velocity and the vapors less encumbered with catalyst fines then passing through one or more cyclonic separation means. In any of these arrangements, gasiform material comprising stripping gas is passed from the cyclonic separation means represented by separator 32 to a plenum chamber 16 for removal with hydrocarbon products of the operation by conduit 18. Gasiform material comprising hydrocarbon vapors is passed by conduit 18 to a product separation equipment 19.

Hot stripped catalyst at an elevated temperature is withdrawn from a lower portion of the stripping zone by conduit 36 for transfer to a dense fluid bed of catalyst in a catalyst regeneration zone, or returned to a previous operation from which it was cascaded as heretofore mentioned. The catalyst may also subsequently be cascaded to a following conversion step and/or cascaded to the inlet of riser 4 for admixture with catalyst from conduit 6. Flow control valve 38 is provided in transfer conduit 36.

In addition, the process can include any combination of the following options:

1. Addition of a processing riser system as a satellite on an existing short contact time FCC unit, with common fractionation system, and with or without common separation/regeneration system; a particularly preferred aspect of this satellite system is that a slip stream of spent catalyst can be taken from reactor to the existing regenerator; an FCC could operate in blocked out operation with one or more chemical-type operations.

2. Provisions for recycle of unconverted reactant or higher boiling alkylaromatics to the riser if desired.

3. Provisions for recycle cascade of partially coked catalysts to regulate catalyst/hydrocarbon ratio or catalyst activity/selectivity.

4. Provisions for multiple injection of reacant(s) along the riser(s).

5. Provisions for fluidized dense bed processing in addition to riser reaction, i.e., provision for longer contact time exposure of reactants, if desired.

6. Inclusion of multiple, separate risers for upgrading of reactants, recycled products or product-reactant combinations, wherein temperature, catalyst/hydrocarbon ratio, residence time, catalyst activity/selectivity/type can be varied to meet the requirements of a particular fraction (or product specification).

7. Regeneration system where a particle density gradient (between two catalyst types of different density) is established in a regenerator, and regenerated catalyst from each of the two (density) zones is returned separately to various positions in risers.

8. Provisions for common or separate cyclone (catalyst/hydrocarbon separation) system.

9. Provisions for common or separate regeneration system.

10. Provisions for using different catalysts in the separate riser systems, or in separate stages of a single riser if desired.

11. Provisions for reactivation of catalyst between regenerator and reactor.

12. Provisions for introduction of promoters such as $H_2O$, $CO_2$, HCl, etc. between regenerator and reactor.

13. Source of heat to get catalyst/reactant temperature to the desired mix temperature can be any one or any combination of the following:
- from feed preheat
- from feed/effluent heat exchange systems
- from regenerated catalyst from this process
- from regenerated catalyst from a large, existing fuels FCC if there is a satellite chemicals reactor
- from burning of torch oil, petroleum coke or other coke in the regenerator with heat transferred to the reactor via the circulating catalyst
- where very low coke level catalyst from this process is cascaded to another reaction system in series with the first, such as gas oil cracking, where additional coke is laid down (thus taking advantage of the residual catalyst activity), and then, the more highly coked catalyst is sent to the regenerator.

DESCRIPTION OF SPECIFIC EMBODIMENTS

As stated above, the catalyst useful in this invention is a porous acid-active zeolite having an FAI of at least about 18. Such zeolites include, among others, acid-active forms of zeolites X, Y, ZSM-5, ZSM-11, ZSM-12, ZSM-35, ZSM-38 and dealuminized mordenite.

Zeolite X is described in U.S. Pat. No. 2,882,244, the disclosure of which is incorporated herein by reference. Zeolite Y is described in U.S. Pat. No. 3,130,007, the disclosure of which is incorporated herein by reference. Dealuminized mordenite for use in the present invention may be one prepared by the method of U.S. Pat. No. 3,551,353, the disclosure of which is incorporated herein by reference. Zeolite ZSM-5 is described in U.S. Pat. No. 3,702,886, the disclosure of which is incorporated by reference. Zeolite ZSM-11 is described in U.S. Pat. No. 3,709,979, the disclosure of which is incorporated herein by reference. Zeolite ZSM-12 is described in U.S. Pat. No. 3,832,449, the disclosure of which is incorporated herein by reference.

ZSM-35 is more particularly described in U.S. Application Ser. No. 528,061, filed Nov. 29, 1974. This zeolite can be identified, in terms of mole ratios of oxides and in the anhydrous state, as follows:

$$(0.3-2.5)R_2O : (0-0.8)M_2O : Al_2O_3 : xSiO_2$$

wherein x is greater than 8, R is an organic nitrogen-containing cation derived from ethylenediamine or pyrrolidine and M is an alkali metal cation, and is characterized by a specified X-ray powder diffraction pattern.

In a preferred synthesized form the zeolite has a formula, in terms of mole ratios of oxides and in the anhydrous state, as follows:

$$(0.4-2.5)R_2O : (0-0.6)M_2O : Al_2O_3 : ySiO_2$$

wherein R is an organic nitrogen-containing cation derived from ethylenediamine or pyrrolidine, M is an alkali metal, especially sodium, and y is from greater than 8 to about 50.

The synthetic ZSM-35 zeolite possesses a definite distinguishing crystalline structure whose X-ray diffraction pattern shows substantially the significant lines set forth in Table I. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5 A. This very weak line, however, is determined not to be a significant line for ZSM-35.

TABLE I

| d(A) | I/Io |
|---|---|
| 9.6 ± 0.20 | Very Strong - Very, Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| | Broad | Preferred |
|---|---|---|
| $R^+/(R^+ + M^+)$ | 0.2–1.0 | 0.3–0.9 |
| $OH^-/SiO_2$ | 0.05–0.5 | 0.07–0.49 |
| $H_2O/OH^-$ | 41–500 | 100–250 |
| $SiO_2/Al_2O_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. The quantity of $OH^-$ is calculated only from the inorganic sources of alkali without any organic base contribution. Thereafter, the crystals are separated from the liquid are recovered. Typical reaction conditions consist of heating the foregoing reaction mixture to a temperature of from about 90° F to about 400° F for a period of time of from about 6 hours to about 100 days. A more preferred temperature range is from about 150° F to about 400° F with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F, for from about 8 to 24 hours.

Zeolite ZSM-38 is more particularly described in U.S. Application Ser. No. 560,412, filed Mar. 20, 1975. This zeolite can be identified, in terms of mole ratios of oxides and in the anhydrous state, as follows:

$$(0.3-2.5)R_2O : (0-0.8)M_2O : Al_2O_3 : xSiO_2$$

wherein x is greater than 8, R is an organic nitrogen-containing cation derived from a 2-(hydroxyalkyl) trialkylammonium compound and M is an alkali metal cation, and is characterized by a specific X-ray powder diffraction pattern.

In a preferred synthesized form, the zeolite has a formula, in terms of mole ratios of oxides and in the anhydrous state, as follows:

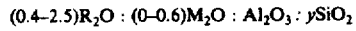

$$(0.4-2.5)R_2O : (0-0.6)M_2O : Al_2O_3 : ySiO_2$$

wherein R is an organic nitrogen-containing cation derived from a 2-(hydroxyalkyl) trialkylammonium compound, wherein alkyl is methyl, ethyl or a combination thereof, M is an alkali metal, especially sodium, and y is from greater than 8 to about 50.

The synthetic ZSM-38 zeolite possesses a definite distinguishing crystalline structure whose X-ray diffraction pattern shows substantially the significant lines set forth in Table II. It is observed that this X-ray diffraction pattern (significant lines) is similar to that of natural ferrierite with a notable exception being that natural ferrierite patterns exhibit a significant line at 11.33A.

TABLE II

| d(A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of both ZSM-35 and ZSM-38 is their sorptive capacity providing them to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for both ZSM-35 and ZSM-38 (after calcination at 600° C) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

|  | Broad | Preferred |
|---|---|---|
| R+/(R+ + M+) | 0.2–1.0 | 0.3–0.9 |
| OH−/SiO$_2$ | 0.05–0.5 | 0.07–0.49 |
| H$_2$O/OH− | 41–500 | 100–250 |
| SiO$_2$/Al$_2$O$_3$ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. The quantity of OH− is calculated only from the inorganic sources of alkali without any organic base contribution. Thereafter, the crystals are separated from the liquid and recovered. Typical reaction conditions consist of heating the foregoing reaction mixture to a temperature of from about 90° F to about 400° F for a period of time of from about 6 hours to about 100 days. A more preferred temperature range is from about 150° F to about 400° F with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F for from about 8 to 24 hours.

The specific zeolites above described, when prepared in the presence of organic cations, are catalytically inactive, possibly because the intracrystalline free space is occupied by organic cations from the forming solution. They may be activated by heating, for example, in an inert atmosphere at 1000° F for 1 hour, followed by base exchange with ammonium salts and by calcination at 1000° F in air. The presence of organic cations in the forming solution may not be absolutely essential to the formation of the type zeolite for use herein; however, the presence of these cations does not appear to favor the formation of said zeolite. More generally, it is desirable to activate the catalyst for use herein by base exchange with ammonium salts followed by calcination in air at about 1000° F for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates for use herein are X, Y, dealuminized mordenite, ZSM-5, ZSM-11, ZSM-12, ZSM-35 and ZSM-38, with ZSM-5 particularly preferred.

The catalysts for use in this invention may be in the hydrogen form or they may be based exchanged or impregnated to contain ammonium or a metal cation complement. It is desirable to calcine the catalyst after base exchange. The metal cations that may be present include any of the cations of the metals of Groups I through VIII of the Periodic Table, especially rare earth metals. However, in the case of Group IA metals, the cation content should in no case be so large as to effectively inactivate the catalyst.

"Fluid activity index" (FAI) is defined as the conversion obtained to provide a 356° F 90% ASTM gasoline product processing a Light East Texas Gas Oil (LETGO) at a 2 catalyst/oil ratio, 850° F, 6 WHSV for 5 minutes on stream time. Conversion is defined as 100-cycle oil product.

As in the case of many catalysts, it is desirable to incorporate the catalyst for use herein with another material resistant to the temperature and other conditions employed in the present process. Such matrix materials include active and inactive materials and synthetic or naturally occurring zeolites as well as inorganic materials such as clays, silica and/or metal oxides.

The latter may be either naturally occurring or in the form of gelatinous precipitates, sols or gels including mixtures of silica and metal oxides. Inactive materials suitably serve as diluents to control the amount of conversion in a given process so that products can be obtained economically and orderly without employing other means for controlling the rate of reaction. Frequently, zeolite materials have been incorporated into naturally occurring clays, e.g. bentonite and kaoline. These materials, i.e. clays, oxides, etc., function, in part, as binders for the catalyst. It is desirable to provide a catalyst having good crush strength, because in the process of this invention the catalyst is subjected to rough handling, which may tend to break the catalyst down into powder-like materials which case problems in processing.

Naturally occurring clays which can be composited with the zeolites for use herein include the montmorillonite and kaoline families, which include the sub-bentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chamical modification.

In addition to the foregoing materials, the zeolites for use herein can be composited with one or more porous matrix materials such as silica-alumina, silica-magnesia, silica-zirconia, silica-thoria, silica-beryllia, silica-titania, titania-zirconia as well as ternary compositions such as silica-alumina-thoria, silica-alumina-zirconia, silica-alumina-magnesia and silica-magnesia-zirconia. The matrix can be in the form of a cogel. A mixture of these components, one with the other and/or with a clay, could also be used. The relative proportions of finely divided porous zeolite having an FAI of at least about 18 for use herein and inorganic oxide gel matrix and/or clay vary widely with the crystalline aluminosilicate content ranging from about 1 to about 90 percent by weight and more usually in the range of about 2 to about 50 percent by weight of the composite.

Reaction conditions under which the invention is conducted may vary with different charge stock compositions within the definition of alkylaromatic hydrocarbon of from 7 to 10 carbon atoms and with differences in design factors of the equipment used in the process. Although the reaction temperature in the present process at the reactor system or riser inlet may be maintained at between about 300° F and about 1200° F, the preferred temperature is from about 500° F to about 1100° F. The broadest applicable reaction pressure useful in the process is from about 0 psig to about 200 psig, with preferred pressure being within the range of from about 10 psig to about 70 psig. The catalyst/hydrocarbon feedstock weight ratio may be maintained within the broad range of from about 1 to about 60, with a preferred catalyst/hydrocarbon feedstock weight ratio of between about 5 and about 40. Catalyst residence time and heavy reformate residence time are also critical factors in this process and may be maintained within the ranges of from about 0.01 second to about 300 seconds and from about 0.01 second to about 300 seconds, respectively, with preferred ranges of from about 0.5 second to about 20 seconds and from about 0.5 second to about 20 seconds, respectively. The preferred slip ratio, hereinabove defined, is within the range of from about 1 to about 1.8.

Exemplary of the alkylaromatic hydrocarbons which may be transalkylated by the present process are alkyl-substituted aromatics such as toluene, durene, xylene and homologs thereof. Transalkylating agents for use herein include, as non-limiting examples, alkyl or polyalkylaromatic hydrocarbons wherein alkyl may be composed of from 1 to about 5 carbon atoms, such as toluene, xylene, trimethylbenzene, triethylbenzene, dimethylethylbenzene, ethylbenzene, diethylbenzene and ethyltoluene.

It is noted that disproportionation is a special case of transalkylation in which the alkylatable aromatic hydrocarbon and the transalkylating agent is the same compound, for example, when toluene serves as the donor and acceptor of a transferred methyl group to produce benzene and xylene. It should be understood that the term transalkylation as used herein includes the special case of disproportionation.

Embodiments of the processing of the present invention are illustrated by the specific examples which follows. It is to be understood that these specific embodiments are illustrative and do not limit the scope of the invention as defined above. Examples 1–5 illustrate preparation of catalyst materials useful in the present process.

EXAMPLE 1

(Catalyst Preparation)

This was a silica-clay-$ZrO_2$ matrix catalyst having a composition 60 weight percent silica and 40 weight percent clay to which was added sufficient sodium zirconium silicate to contribute 2 weight percent $ZrO_2$.

The catalytic composition was prepared by slurrying 4.97 pounds of Georgia Kaoline clay (85.8 weight percent solids on dry basis) into 95.55 pounds of water. To this slurry was then added 21.975 pounds of Q-Brand sodium silicate (28.9 weight percent $SiO_2$, 8.9 weight percent $Na_2O$, 62.2 weight percent $H_2O$) which was heated to 120° F. The slurry was then heated to 120° F and acidified with 500 cc concentrated $H_2SO_4$ followed with heating to and holding at 140° F for 2 hours. During all of the processing the slurry was mixed vigorously in a batch tank with continuous recirculation to insure good dispersion. To the aged heat treated slurry was then added 276 grams of a sodium zirconium silicate dispersed in 3 liters of water containing 180 cc of concentrated $H_2SO_4$. This amount of sodium zirconium silicate constituted an addition of 2 weight percent $ZrO_2$ to the matrix. The slurry was further acidified to 4.5 pH by the addition of 169.6 cc of concentrated $H_2SO_4$ and allowed to stand overnight while being mixed slowly.

To the aged acidified slurry was added 34.8 cc of 50 percent KOH solution to adjust the pH to 4.5 prior to the addition of the zeolites. The zeolite components were made up of 125 grams of REY (rare earth exchanged Y zeolites to 2.9 weight percent residual sodium commercially calcined to about 1000°–1200° F) along with 699 grams of hydrogen-exchanged mordenite dispersed in 220 cc water with 7.5 grams of Marasperse "N", a dispersing agent. These zeolitic components were first dispersed in a high shear mixer followed by three passes in a colloid mill before addition to the clay silicate slurry. The REY component constituted 2 weight percent of the final composition and the mordenite constituted 10 weight percent of the final composition.

The final slurry containing the zeolite componets was sprayed dried with an inlet air temperature of 865°-895° F and an exit air temperature of 325° F.

The spray dried product was slurried in water, then base exchanged with a 5 weight percent $(NH_4)_2SO_4$ solution at room temperature. The exchange solution consisted of 15 gallons of solution charged over about 5 pounds of catalyst during a 5 hour period. The exchanged catalyst was then water washed free of sulfate ion; contacted with 1% $RECl_3.6H_2O$ solution; filtered; dried at 340° F; then steamed for 4 hours at 1400° F with 100% steam at atmospheric pressure.

The final steamed product containing 2 weight percent REY and 10 weight percent mordenite had a residual sodium content of 0.03 weight percent and a surface area of 205 m²/gram. The FAI of this catalyst composition proved to be 38.6.

EXAMPLE 2

(Catalyst Preparation)

This catalyst, a silica-clay-$ZrO_2$ matrix containing 10 weight percent aluminum defficient mordenite was prepared essentially in the same manner as described in Example 1. The aluminum deficient mordenite was prepared by treating 4.5 pounds of hydrogen-exchanged mordenite with a 2.07 weight percent HCl solution, using 7.5 grams solution/gram of mordenite, for 2 hours at 146° F. This process was repeated twice more at 165° F with decantation between each contact. The final contact was followed with water washing free of chloride ion, drying at 340° F, calcining for 10 hours at 1000° F and steam treating for 16 hours at 1000° F with 100% steam. The steamed material was then retreated with HCl as described above followed by water washing, drying and calcining. The silica/alumina molar ratio of the aluminum deficient mordenite was 40/1.

The catalyst of this example as described above was used in both calcined (10 hours at 1000° F) and steamed form (4 hours at 1400° F). The surface area of the calcined form was 282 m²/gram and the steamed form was 198 m²/gram. The FAI of the calcined form was 44.6. The FAI of the steamed form was 19.2.

EXAMPLE 3

(Catalyst Preparation)

This catalyst, a silica-clay-$ZrO_2$ matrix catalyst, was prepared essentially as described in Example 1, incorporating sufficient amount of HZSM-5 to constitute 10% HZSM-5 in final composition. The HZSM-5 used in this catalyst was prepared by precalcining, 3 hours at 1000° F in $N_2$, a sodium nitrogen ZSM-5 then exchanging with $NH_4Cl$ solution, followed by water washing chloride free and incorporating into the matrix. The silica/alumina molar ratio of the HZSM-5 component was 70/1.

The final fluid catalyst was used in the calcined form (10 hours at 1000° F). It proved to have an FAI of 42.6.

EXAMPLE 4

(Catalyst Preparation)

This fluid catalyst was prepared to contain 20 weight percent HZSM-5 in a silica-alumina (13 weight percent $Al_2O_3$) matrix.

The particular ZSM-5 used in this composition was prepared by interacting the following solutions:

Silicate Solution 90.9 pounds of Q-Brand sodium silicate (28.9 weight percent $SiO_2$, 8.9 weight percent $Na_2O$, 62.2 weight percent $H_2O$)
52.6 pounds of $H_2O$ (26.3 pounds of ice)
0.266 pounds of Daxad dispersing agent
Specific Gravity 1.226 at 60.

Acid Solution 54 pounds of water (27 pounds of ice)
6.3 pounds of $Al_2(SO_4)_3 \cdot XH_2O$
4.06 pounds of NaCl
6.0 pounds of $H_2SO_4$
Specific Gravity 1.147 at 60
12.95 pounds of NaCl and 2.6 pounds of water added to autoclave.

These solutions are nozzle mixed together at a rotometer indication of 83% silicate and 44% acid solution and charged directly to a 30 gallon autoclave. The mixture was then whipped for 1 hour at 90 RPM. The autoclave was tested for leaks. Then addition thereto was made of the following organics:

10.9 pounds of n-propylamine
5.28 pounds of n-propylbromide
10.1 pounds of methylethylketone The autoclave was then sealed and heated to 220° F (no agitation) and held at that temperature for 6 hours. After this initial reaction period the agitation was started and reactants heated to 210°-230° F and held at 210°-230° F for 7 days. At the end of this period the product was 85% crystalline ZSM-5. The reactants were then heated to 300° F to flash off the unreacted organics and cooled to room temperature. This product slurry was subsequently used as the source of ZSM-5 in the preparation of the silica-alumina matrix catalyst containing 20 weight percent ZSM-5.

In preparing the catalyst composite, the following solutions and procedure were used. Two hundred sixty-two pounds of water was charged to a 30-gallon mixing drum. To this was then added 52.3 pounds Q-Brand (28.9 weight percent $SiO_2$, 8.9 weight percent $Na_2O$, 62.2 weight percent $H_2O$). This solution was acidified with 1253 cc $H_2SO_4$ (95.9 weight percent) to a pH of 10.0 and allowed to react for 45 minutes. To this was then added 6048 grams $Al_2(SO_4)_3 \cdot XH_2O$ in 52.9 pounds of $H_2O$, introducing 13 weight percent $Al_2O_3$ and acidified silicate solution. The pH was finally adjusted to 4.5 with the addition of 50% NaOH solution. To the 4.5 pH slurry was then added 1983 grams of ZSM-5, prepared as described above, dispersed in 6000 cc of water.

The composite was spray dried in a countercurrent spray dryer, then exchanged with 20 gallons of 5% $(NH_4)_2SO_4$ solution followed by water washing free of sulfate ion.

The final product was calcined for 3 hours at 1200° F with air in a fluidized bed. The FAI of this catalyst proved to be 51.98.

EXAMPLE 5

(Catalyst Preparation)

This catalyst was a silica-clay-alumina-zirconia matrix catalyst containing 15 weight percent added REY. The catalytic composite was prepared by first dispersing 774 pounds (dry basis) of Georgia Kaolin clay in 19,810 pounds (2390 gallons) of deionized water and thoroughly mixing. To this was added, over 30 minutes, 3861 pounds (334 gallons) Q-Brand sodium silicate (28.9 weight percent $SiO_2$, 8.9 weight percent $Na_2O$, 62.2 weight percent $H_2O$). It was then heated to 120° F. Aqueous 35 weight percent $H_2SO_4$ was then added to adjust the pH to 9.8 and it was aged at this temperature to produce a fluid catalyst having a pore volume of 0.65 to 0.71 cc/gram (approximately 1 hour). An aluminum sulfate solution was then added to contribute 12 pounds of $Al_2O_3$ to the batch. In addition a slurry of 84 pounds sodium zirconium silicate (45 weight percent $ZrO_2$), dispersed in 6.7 gallons of 66° Baume sulfuric acid and 95 gallons of deionized water, was added over a 45 minute period. While under agitation, additional acid (35% $H_2SO_4$) or 50% NaOH was added to adjust pH to 4.5–4.6.

To the acidified silica-clay-$Al_2O_3$-$ZrO_2$ matrix slurry was added the rare earth Y as a slurry of 342 pounds (dry basis) of rare earth Y dispersed in 125 gallons of water. This slurry was pumped into the tank containing the matrix slurry and mixed extensively to insure uniformity.

The resulting slurry was dewatered on a belt filter to about 10–15 weight percent solids prior to spray drying.

The spray dried product was ion-exchange with ammonium sulfate solution to reduce the residual sodium to 0.2 weight percent. Subsequently, the exchanged spray dried product was contacted with $RECl_3.6H_2O$ solution to deposit approximately 3 weight percent additional $(RE)_2O_3$ in the catalyst. The treated catalyst was then flash dried to a solids content of about 85% at 1800° F.

The composition of the fluid catalyst which had an FAI of 67.5 was as follows:

| | |
|---|---|
| $Na_2O$ | 0.2 weight percent |
| $SO_4$ | 0.5 weight percent |
| $(RE)_2O_3$ | 4.9–5.3 weight percent |
| $Al_2O_3$ | 17–19 weight percent |
| Fe | 0.15 weight percent |
| $ZrO_2$ | 1.6–1.9 weight percent |

EXAMPLES 6–17

Experiments were conducted in a 30-foot bench scale FCC riser unit (Examples 6–14) and in a 6.12-foot bench scale FCC riser unit (Examples 15–17) to demonstrate the present process. An alkylaromatic feedstock and a transalkylating agent, each being toluene, were contacted in accordance herewith at various conditions and over various catalysts. In general, the toluene was pumped to the inlet of the riser, preheated and admitted to the riser inlet, where hot catalyst was also admitted. Effluent obtained from the unit was then passed through a stripping chamber where gaseous effluent was separated from spent catalyst. The gaseous effluent was then cooled and liquid product was collected. The liquid product was then separated by fractionation and analyzed. Variables which were measured or calculated and which appear in Tables III–VIII hereinafter are reactor inlet temperature, hydrocarbon inlet temperature, catalyst inlet temperature, mix temperature, catalyst/hydrocarbon weight ratio, catalyst residence time, hydrocarbon residence time, riser inlet pressure, hydrocarbon partial pressure, moles of product/mole of feedstock, amount of carbon on spent catalyst and product composition.

TABLE III

| | TOLUENE DISPROPORTIONATION | | | | |
|---|---|---|---|---|---|
| Example | 6 | 7 | 8 | 9 | 10 |
| Reaction Conditions | | | | | |
| Reactor Inlet Temperature, ° F | 800 | 900 | 900 | 900 | 900 |
| Hydrocarbon Inlet Temperature, ° F | 500 | 500 | 500 | 500 | 500 |
| Catalyst Inlet Temperature, ° F | 1027 | 991 | 991 | 991 | 991 |
| $T_{mix}$ ° E | 807 | 871 | 869 | 882 | 865 |
| Catalyst/Hydrocarbon (wt/wt) Ratio | 3.86 | 8.49 | 8.39 | 9.66 | 8.02 |
| Catalyst Residence Time, sec. | 2.71 | 3.85 | 6.73 | 6.69 | 6.84 |
| Hydrocarbon Residence Time, sec | 2.20 | 3.13 | 5.34 | 5.35 | 5.43 |
| Riser Inlet Pressure, psig | 30.0 | 30.0 | 30.0 | 30.0 | 30.0 |
| Hydrocarbon Partial Pressure, psia | 38.6 | 37.0 | 32.9 | 32.8 | 33.2 |
| Moles of Product/Mole of Feed (ex coke) | 0.92 | 0.92 | 0.92 | 0.93 | 0.92 |
| Carbon, Spend Catalyst, % Wt. | 0.037 | 0.058 | 0.031 | 0.000 | 0.01 |
| Slip Ratio | 1.23 | 1.23 | 1.26 | 1.25 | 1.26 |
| Catalyst of Example | 1 | 5 | 2 | 2 | 3 |
| | | | | (steamed) | |
| Mass Balance, Wt.% | | | | | |
| $C_6^+$ Liquid | 99.42 | 98.95 | 98.96 | 99.12 | 99.25 |
| $C_3$'s | .17 | .13 | .25 | .45 | .17 |
| $C_4$- Gas | .26 | .38 | .50 | .43 | .44 |
| Coke | .16 | .54 | .29 | .00 | .09 |
| Recovery | 96.3 | 98.3 | 94.1 | 92.4 | 96.6 |

TABLE IV

| | TOLUENE DISPROPORTIONATION | | | |
|---|---|---|---|---|
| Example | 11 | 12 | 13 | 14 |
| Reaction Condition | | | | |
| Reactor Inlet Temperature, ° F | 1100 | 1100 | 1100 | 1100 |
| Hydrocarbon Inlet Temperature, ° F | 600 | 500 | 500 | 500 |
| Catalyst Inlet Temperature, ° F | 1218 | 1157 | 1157 | 1157 |
| $T_{mix}$ ° F | 1067 | 1075 | 1072 | 1073 |
| Catalyst/Hydrocarbon (wt/wt) Ratio | 8.51 | 19.30 | 18.5 | 18.83 |
| Catalyst Residence Time, sec. | 2.78 | 12.10 | 16.71 | 10.34 |
| Hydrocarbon Residence Time, sec | 2.34 | 9.53 | 13.16 | 8.14 |

TABLE IV-continued

TOLUENE DISPROPORTIONATION

| Example | 11 | 12 | 13 | 14 |
|---|---|---|---|---|
| Riser Inlet Pressure, psig | 30.0 | 40.0 | 40.0 | 40.0 |
| Hydrocarbon Partial Pressure, psia | 37.8 | 26.9 | 34.1 | 22.9 |
| Moles of Product/Mole of Feed (ex coke) | 0.92 | 0.95 | 0.92 | 0.94 |
| Carbon, Spent Catalyst, % Wt. | 0.071 | 0.061 | 0.208 | 0.009 |
| Slip Ratio | 1.19 | 1.27 | 1.27 | 1.27 |
| Catalyst of Example | 5 | 2 | 5 | 3 |
| Mass Balance, Wt.% | | | | |
| $C_6{}^{30}$ Liquid | 98.76 | 97.32 | 93.04 | 98.80 |
| $C_5$'s | .08 | .42 | .30 | .53 |
| $C_4{}^-$ Gas | .50 | .99 | 2.50 | .48 |
| Coke | .67 | 1.28 | 4.16 | .18 |
| Recovery | 92.9 | 90.9 | 100.2 | 93.3 |

TABLE V

TOLUENE DISPROPORTIONATION

| Example | 15 | 16 | 17 |
|---|---|---|---|
| Reaction Conditions | | | |
| Reactor Inlet Temperature, °F | 1000 | 1200 | 1200 |
| Hydrocarbon Inlet Temperature, °F | 797 | 791 | 787 |
| Catalyst Inlet Temperature, °F 1036 | 1290 | 1216 | |
| $T_{min}$ °F | 980 | 1187 | 1165 |
| Catalyst/Hydrocarbon (wt/wt) Ratio | 9.06 | 10.61 | 7.04 |
| Catalyst Residence Time, sec | 1.43 | 1.31 | 1.25 |
| Hydrocarbon Residence Time, sec | 0.80 | 0.73 | 0.69 |
| Riser Inlet Pressure, psig | 30.0 | 30.0 | 30.0 |
| Hydrocarbon Partial Pressure, psia | 37.0 | 37.3 | 38.6 |
| Moles of Product/Mole of Feed (ex coke) | 0.96 | 0.93 | 0.98 |
| Carbon, Spent Catalyst, % Wt. | 0.051 | 0.20 | 0.039 |
| Slip Ratio | approx. 1.8 | approx. 1.8 | approx. 1.8 |
| Catalyst of Example | 5 | 5 | 4 |
| Mass Balance, Wt.% | | | |
| $C_6{}^+$ Liquid | 96.28 | 95.37 | 95.19 |
| $C_5$'s | .35 | .28 | 1.09 |
| $C_4{}^-$ Gas | 2.89 | 2.11 | 3.43 |
| Coke | .49 | 2.24 | .29 |
| Recovery | 97.4 | 98.1 | 98.1 |

TABLE VI

TOLUENE DISPROPORTIONATION

| Example | 6 | 7 | 8 | 9 | 10 |
|---|---|---|---|---|---|
| Conversion, Toluene, Wt.% | | | | | |
| To all other products | 1.0 | 13.1 | 16.8 | 2.2 | 0.6 |
| To other aromatics | 0.5 | 12.2 | 16.0 | 1.8 | 0.1 |
| Selectivity for Liquid Aromatics | 50.0 | 93.1 | 95.2 | 81.8 | 16.7 |
| Liquid Product Breakdown, Wt.% | | | | | |
| $C_5{}^-$ | .04 | .03 | .01 | — | — |
| Benzene | .13 | 4.83 | 7.30 | 0.85 | — |
| Toluene | 99.46 | 87.69 | 83.86 | 98.22 | 99.9 |
| Ethylbenzene | .04 | .06 | .06 | .06 | |
| p-Xylene | .13 | 1.68 | 2.23 | .41 | |
| m-Xylene | .15 | 3.41 | 4.39 | .34 | .1 |
| o-Xylene | .04 | 1.51 | 1.91 | .13 | |
| $C_9{}^+$ Aromatics | — | .79 | .22 | — | |

| Xylene Isomer Breakdown, Wt.% vs Equilibrium | Obs | Eq | Obs | Eq | Obs | Eq | Obs | Eq |
|---|---|---|---|---|---|---|---|---|
| para-Xylene | 40.3 | 23.4 | 25.4 | 23.2 | 26.1 | 23.2 | 46.7 | 23.2 |
| meta-Xylene | 48.5 | 52.3 | 51.7 | 51.8 | 51.4 | 51.8 | 38.6 | 51.8 |
| ortho-Xylene | 11.2 | 24.3 | 22.9 | 25.0 | 22.5 | 25.0 | 14.7 | 25.0 |

TABLE VII

TOLUENE DISPROPORTIONATION

| Example | 11 | 12 | 13 | 14 |
|---|---|---|---|---|
| Conversion, Toluene, Wt.% | | | | |
| To all other products | 20.8 | 32.5 | 52.4 | 3.9 |
| To other aromatics | 19.6 | 30.2 | 45.7 | 3.3 |
| Selectivity for Liquid Aromatics | 94.2 | 92.9 | 87.2 | 84.6 |
| Liquid Product Breakdown, Wt.% | | | | |
| $C_5{}^-$ | .03 | .3 | — | — |
| Benzene | 8.57 | 12.6 | 24.1 | 1.3 |
| Toluene | 80.15 | 69.1 | 51.0 | 96.7 |
| Ethylbenzene | .07 | .0 | .4 | — |
| p-Xylene | 2.43 | 3.8 | 4.4 | .4 |
| m-Xylene | 5.11 | 8.8 | 11.4 | 1.1 |
| o-Xylene 2.46 | 4.4 | 5.2 | .5 | |
| $C_9{}^+$ Aromatics | 1.19 | 1.0 | 3.5 | — |

| Xylene Isomer Breakdown, Wt.% vs Equilibrium | Obs | Eq | Obs | Eq | Obs | Eq | Obs | Eq |
|---|---|---|---|---|---|---|---|---|

TABLE VII-continued

| | TOLUENE DISPROPORTIONATION | | | | | | | |
|---|---|---|---|---|---|---|---|---|
| Example | 11 | | 12 | | 13 | | 14 | |
| para-Xylene | 24.3 | 22.8 | 22.4 | 22.8 | 21.0 | 22.8 | 20.0 | 22.8 |
| meta-Xylene | 51.1 | 50.5 | 51.8 | 50.5 | 54.3 | 50.5 | 55.0 | 50.5 |
| ortho-Xylene | 24.6 | 26.7 | 25.9 | 26.7 | 24.8 | 26.7 | 25.0 | 26.7 |

TABLE VIII

| | TOLUENE DISPROPORTIONATION | | | | |
|---|---|---|---|---|---|
| Example | 15 | | 16 | | 17 |
| Conversion, Toluene, Wt.% | | | | | |
| To all other products | 8.8 | | 17.4 | | 6.3 |
| To other aromatics | 3.7 | | 13.0 | | 2.6 |
| Selectivity for Liquid Aromatics | 42.0 | | 74.7 | | 41.3 |
| Liquid Product Breakdown, Wt.% | | | | | |
| C5- | — | | — | | — |
| Benzene | 1.7 | | 6.7 | | 1.0 |
| Toluene | 96.2 | | 86.4 | | 97.3 |
| Ethylbenzene | — | | .1 | | — |
| p-Xylene | .5 | | 1.5 | | 0.1 |
| m-Xylene | .9 | | 3.2 | | 0.6 |
| o-Xylene | .4 | | 1.5 | | 0.2 |
| $C_9^+$ Aromatics | .1 | | .6 | | — |
| Xylene Isomer Breakdown, Wt% vs | | | | | |
| Equilibrium | Obs | Eq | Obs | Eq | |
| para-Xylene | 27.8 | 23.1 | 24.2 | 22.5 | |
| meta-Xylene | 50.0 | 51.0 | 51.6 | 50.0 | |
| ortho-Xylene | 22.2 | 25.8 | 24.2 | 27.4 | |

It is readily observed from the above specific examples 6-17 that by the present process a highly selective transalkylation, e.g. disproportionation, of an alkylaromatic hydrocarbon compound of from 7 to 10 carbon atoms, e.g. toluene, is provided. The substantially higher selectivity for p-Xylene in toluene disproporation hereby will allow lower costs for cryogenic separation of p-Xylene from m-/p-mixtures. Other benefits are readily apparent. In addition, the small quantity of gas formed in the operation of the present process is excellent alkylation plant feed.

EXAMPLES 18-19

A feedstock consisting of a mixture of durene (20 weight percent) benzene (20 weight percent) and toluene (60 weight percent) was prepared. The mixture had a specific gravity of 0.8732 at 60° F. The durene used in the mixture was 98 percent pure, has a molecular weight of 134.22 and a melting point of 78°-80° C. The mixture of benzene and toluene in the feedstock for these examples simulates a light aromatic gasoline fraction.

In Example 18, the feed mixture was preheated to 423° F and then admitted to the 30-foot bench riser unit utilized above for contact with hot (900° F) catalyst from Example 5. The riser reactor inlet mix temperature was about 800° F. In Example 19, the feed mixture was preheated to 500° F and then admitted to the 30-foot bench riser unit for contact with hot (1006° F) catalyst from Example 5. The riser reactor inlet mix temperature in Example 19 was about 900° F. All reaction conditions for Examples 18 and 19 are listed in Table IX.

The vaporous effluent from each experiment was separated from the catalyst by conventional means. The spent catalyst contained 0.07 weight percent carbon. The effluent was cooled and separated into gaseous and liquid products and analyzed. Tables X and XI contain analysis of product selectively data and gasoline analysis data, respectively.

TABLE IX

| REACTION OF DURENE WITH LOW BOILING AROMATICS | | |
|---|---|---|
| Example | 18 | 19 |
| Reaction Conditions | | |
| Reactor Inlet Temperature, ° F | 800 | 900 |
| Hydrocarbon Feed Temperature, ° F | 423 | 500 |
| Catalyst Inlet Temperature, ° F | 900 | 1006 |
| Catalyst/Hydrocarbon (wt/wt) Ratio | 10.12 | 7.51 |
| Catalyst Residence Time, sec | 4.25 | 4.64 |
| Reactor Inlet Pressure, psig | 30 | 30 |
| Moles of Product/Mole of Feed (ex coke) | 0.924 | 0.920 |
| Hydrocarbon Partial Pressure, psia | 34.9 | 37.8 |
| $T_{mix}$ ° F | 798 | 870 |
| Carbon, Spent Catalyst, % Wt. | 0.07 | 0.118 |
| Slip Ratio | 1.20 | 1.23 |
| Hydrocarbon Residence Time, sec | 3.54 | 3.77 |

TABLE X

| REACTION OF DURENE WITH LOW BOILING AROMATICS ANALYSIS OF PRODUCT SELECTIVITIES | | | | |
|---|---|---|---|---|
| Example | 18 | | 19 | |
| Product Out | Weight Percent Product (No Loss Basis on Feed) | | | |
| Coke | 0.77 | | 0.96 | |
| $C_5^+$ Gasoline | 98.72 | | 98.67 | |
| Gas | 0.51 | | 0.36 | |
| | 100.00 | | 99.99 | |
| Light Product Breakdown | | Wt.% on Gas | | Wt.% on Gas |
| $H_2$ | 0.00 | — | 0.00 | — |
| Methane | 0.01 | 2.0 | 0.03 | 8.1 |
| Ethylene | 0.03 | 5.9 | 0.03 | 8.1 |
| Ethane | 0.00 | — | 0.01 | 2.7 |
| Propylene | 0.04 | 7.8 | 0.02 | 5.4 |
| Propane | 0.10 | 19.6 | 0.07 | 18.9 |

TABLE X-continued

REACTION OF DURENE WITH LOW BOILING AROMATICS ANALYSIS OF PRODUCT SELECTIVITIES

| Example | 18 | | 19 | |
|---|---|---|---|---|
| Butene | 0.10 | 19.6 | 0.06 | 16.2 |
| Isobutane | 0.23 | 45.1 | 0.12 | 32.4 |
| n-butane | 0.00 | — | 0.03 | 8.1 |
| Pentene | 0.05 | 100.0 | 0.02 | 99.9 |
| Isopentane | 0.14 | | 0.08 | |
| n-Pentane | 0.00 | | 0.01 | |
| Recovery, wt.% | 96.02 | | 95.93 | |

TABLE XI

REACTION OF DURENE WITH LOW BOILING AROMATICS : GASOLINE ANALYSIS

| | | Weight Percent | |
|---|---|---|---|
| Type Analysis | Feed | Example 18 | Example 19 |
| Paraffins | | 0.118 | 0.068 |
| Naphthenes | | 0.003 | 0.003 |
| Aromatics | 100.0 | 99.879 | 99.928 |
| Olefins | | 0.000 | 0.000 |
| | | 100.00 | 99.999 |
| Aromatic Breakdown, Wt.% of Gasoline | | | |
| Benzene | 20.0 | 16.64 | 16.95 |
| Toluene | 60.0 | 44.80 | 43.93 |
| Ethyl benzene | | .45 | 0.10 |
| para-xylene | | 6.22 | 7.53 |
| meta-xylene | | 12.68 | 12.99 |
| ortho-xylene | | 5.91 | 6.31 |
| Cumene | | .09 | 0.34 |
| 1,3,5-Trimethylbenzene | | 2.86 | 2.61 |
| 1,2,4-Trimethylbenzene | | 7.23 | 6.66 |
| 1,2,3-Trimethylbenzene | | 1.04 | 1.00 |
| Other $C_9$ alkylbenzenes | | .12 | .11 |
| Durene | 20.0 | .41 | .20 |
| Other Tetramethylbenzenes | | .99 | .68 |
| Other $C_{10}$ Alkylaromatics | | .03 | .01 |
| Other Aromatics | | .30 | .42 |
| | 100.0 | 99.8 | 99.8 |

| Comparison of Xylene Isomer | Example 18 | | Example 19 | |
|---|---|---|---|---|
| Distribution with Equilibrium | Observed | Eq. 800° F | Observed | Eq. 900° F |
| p-Xylene | 25.1 | 23.3 | 28.1 | 23.2 |
| m-Xylene | 51.1 | 52.2 | 48.4 | 51.7 |
| o-Xylene | 23.8 | 24.3 | 23.5 | 25.0 |
| | 100.0 | 99.8 | 100.0 | 99.9 |

The durene in Examples 18 and 19 represents a troublesome $C_{10}$-alkylbenzene (1,2,4,5-tetramethylbenzene), which is sometimes formed in significant quantities in the conversion of methanol to gasoline. Durene raises the pour point of the gasoline, will crystallize out at low temperatures and thus act as a sludge, potentially plugging pipes, filters, etc. In the present experiments, the above mixture of durene, benzene and toluene was converted in a bench scale riser FCC to a substantially durene-free, high-quality gasoline product with only a trace loss of carbon to gas or coke.

In both riser runs, the level of durene in the gasoline product was reduced from a level of about 20 weight percent to levels of about 0.2–0.4 weight percent, a decrease by a factor of 500–100. That is, durene in the gasoline product was lowered to insignificant trace levels by the single pass fluid catalyst riser conversion operation at short contact time. The presence of durene at such low levels will not cause problems such as crystallization or precipitation which could lead to mechanical problems in transfer lines.

Further, the redistribution of alkyl groups in the reactant mixture was catalytically effected with essentially 98–99 weight percent conservation of carbon as aromatic gasoline, with less than 1 weight percent of total feed going to coke and less than about 0.5 weight percent of the total feed going to gas. That is, in this fuels-oriented transformation, virtually no loss of valuable, high-octane alkyl aromatics to gas or coke was observed.

Surprisingly, the separated gas product from Examples 18 and 19 is potentially a valuable product, since it consisted of only a minor proportion of methane, and large amounts of $C_2$-$C_5$ olefins plus a preponderance of isobutane. The molecular distribution obtained at 800° F is particularly useful. Such a product stream is an excellent acid alkylation plant feed, with more than enough isobutane for alkylation stoichiometry.

A numerical analysis of the data in Table XI suggests that much of the xylene in the products of Examples 18 and 19 came from transalkylation of toluene with methyl fragments from durene and/or trimethylbenzenes, with another moderately large contribution deriving from the demethylation cascade durene $\xrightarrow{-CH_3}$ trimethylbenzene $\xrightarrow{-CH_3}$ xylene. Almost half the trimethylbenzenes formed from initial durene transalkylation further reacted to form xylenes from reaction with toluene (and benzene, to a minor extent).

It is also noted that significantly higher amounts of p-xylene (at expense of both o- and m-xylene) resulted in these runs (25–28% vs 23.3% Eq.). This is significant in terms of improved cryogenicxylene isomer separation.

EXAMPLES 20-24

In the same reactor used for transalkylation, i.e. disproportionation, of toluene, another feedstock alkylaromatic hydrocarbon compound, i.e. o-xylene, was processed in accordance herewith in the same way. Tables XII and XIII list reaction conditions, mass balances, light product analyses and liquid product analyses for Examples 20-24. The reactions of these examples showed low coke and gas formation and high activity. The extent of xylene isomerization in these short contact time, low catalyst/hydrocarbon ratio, morderate temperature experiments was slight, with most of the conversion being to the m-isomer.

TABLE XII

| | CONVERSION OF O-XYLENE | | | | |
|---|---|---|---|---|---|
| Example | 20 | 21 | 22 | 23 | 24 |
| Reaction Conditions | | | | | |
| Reactor Inlet Temperature, °F | 600 | 700 | 700 | 800 | 800 |
| Hydrocarbon Inlet Temperature, °F | 500 | 500 | 500 | 500 | 500 |
| Catalyst Inlet Temperature, °F | 640 | 893 | 893 | 1089 | 1089 |
| $T_{mix}$, °F | 609 | 700 | 700 | 800 | 800 |
| Catalyst/Hydrocarbon (wt/wt) Ratio | 9.69 | 2.28 | 2.36 | 2.44 | 2.70 |
| Catalyst Residence Time, sec | 7.38 | 2.81 | 5.42 | 2.83 | 5.36 |
| Hydrocarbon Residence Time, sec | 5.90 | 2.25 | 4.33 | 2.26 | 4.29 |
| Riser Inlet Pressure, psig | 30.0 | 30.0 | 30.0 | 30.0 | 30.0 |
| Hydrocarbon Partial Pressure, psia | 27.1 | — | — | — | — |
| Moles of Product/Mole of Feed (ex coke) | 1.074 | — | — | — | — |
| Carbon, Spent Catalyst, % Wt | .048 | .0604 | .0774 | 0869 | .0671 |
| Slip Ratio | 1.25 | 1.25 | 1.25 | 1.25 | 1.25 |
| Catalyst of Example | 2 | 5 | 5 | 5 | 5 |
| Mass Balance, Wt.% | | | | | |
| $C_6^+$ Liquid | 98.41 | 99.83 | 99.79 | 99.69 | 99.77 |
| $C_5^-$ Gas | 1.08 | .02 | .02 | .06 | .03 |
| Coke | .51 | .15 | .19 | .25 | .20 |
| Recovery | 95.76 | 95.73 | 97.35 | 88.0 | 94.64 |

TABLE XIII

| | CONVERSION OF O-XYLENE | | | | | | | | | |
|---|---|---|---|---|---|---|---|---|---|---|
| Example | 20 | | 21 | | 22 | | 23 | | 24 | |
| Conversion, o-Xylene, Wt. % | | | | | | | | | | |
| To all other products | 21.87 | | 12.70 | | 17.01 | | 36.32 | | 38.47 | |
| To other aromatics | 20.28 | | 12.54 | | 16.80 | | 36.01 | | 38.24 | |
| Selectivity for Liquid Aromatics | 92.73 | | 98.7 | | 98.8 | | 99.1 | | 99.4 | |
| Ratio, Isom/Transalkylate* | 1.49 | | 1.17 | | 1.32 | | 1.31 | | 1.38 | |
| Liquid Product Breakdown, Wt. % | | | | | | | | | | |
| $C_5^-$ | .00 | | .00 | | .05 | | .02 | | .00 | |
| Benzene | .08 | | .08 | | .08 | | .18 | | .15 | |
| Toluene | 1.78 | | 2.37 | | 2.77 | | 6.25 | | 6.42 | |
| Ethylbenzene | .17 | | .01 | | .10 | | .06 | | .04 | |
| p-Xylene | 1.02 | | .66 | | .79 | | 2.38 | | 2.32 | |
| m-Xylene | 11.24 | | 6.10 | | 8.66 | | 18.03 | | 19.87 | |
| o-Xylene | 79.39 | | 87.44 | | 83.16 | | 63.88 | | 61.67 | |
| Trimethylbenzenes | .18 | | .82 | | 3.45 | | 8.31 | | 8.66 | |
| Other $C_9$- Alkylbenzenes | | | 2.33 | | .06 | | .09 | | .09 | |
| $C_{10}^+$ Aromatics | 6.14 | | .11 | | .70 | | .71 | | .69 | |
| | 100.0 | | 99.92 | | 99.82 | | 99.91 | | 99.91 | |
| Xylene Isomer Breakdown, Wt. % vs | | | | | | | | | | |
| Equilibrium | Obs | Eq | Obs | Eq | Obs | Eq | Obs | Eq | Obs | Eq |
| para-Xylene | 1.1 | 23.8 | .70 | 23.6 | .85 | 23.6 | 2.82 | 23.4 | 2.77 | 23.4 |
| meta-Xylene | 12.3 | 53.3 | 6.48 | 53.0 | 9.35 | 53.0 | 21.39 | 52.3 | 23.70 | 52.3 |
| ortho-Xylene | 86.6 | 22.8 | 92.81 | 23.4 | 89.80 | 23.4 | 75.78 | 24.3 | 73.54 | 24.3 |

*Ratio, weight percent o-Xylene isomerized to m- plus p-Xylene/weight percent o-Xylene transalkylated It will be appreciated that the operating conditions for the transalkylation reaction in accordance with the process of this invention, as exemplified in the foregoing examples, may be varied within the limits specified and that various modifications and alterations may be made in the process of this invention without departing from the spirit and scope thereof.

What is claimed is:

1. In a process for effecting transalkylation of an alkylaromatic hydrocarbon compound having from 7 to 10 carbon atoms which comprises contacting said alkylaromatic hydrocarbon compound with a transalkylating agent in the presence of a porous acid-active zeolite catalyst and in the absence of added hydrogen, the improvement wherein said catalyst has a fluid activity index of at least 18 and said contacting is conducted in a fluidized catalyst system reactor under conditions effective for accomplishing said transalkylation including a reactor inlet temperature of between about 300° F and about 1200° F, a reactor pressure of between about 0 psig and about 200 psig, a catalyst/alkylaromatic hydrocarbon compound weight ratio of between about 1 and about 60, a catalyst residence time of between about 0.01 second and about 20 seconds, an alkylaromatic hydrocarbon compound residence time of between about 0.01 second and about 20 seconds and a ratio of catalyst residence time/alkylaromatic hydrocarbon compound residence time of from about 1 to about 2.

2. The process of claim 1 wherein said fluidized catalyst system is a riser/transport system.

3. The process of claim 1 wherein said catalyst is a zeolite selected from the group consisting of X, Y, ZSM-5, ZSM-11, ZSM-12, ZSM-35, ZSM-38 and dealuminized mordenite.

4. The process of claim 2 wherein the catalyst is a zeolite selected from the group consisting of X, Y, ZSM-5, ZSM-11, ZSM-12, ZSM-35, ZSM-38 and dealuminized mordenite.

5. The process of claim 3 wherein the catalyst is zeolite Y.

6. The process of claim 4 wherein said catalyst is zeolite Y.

7. The process of claim 3 wherein said catalyst is dealuminized mordenite.

8. The process of claim 4 wherein said catalyst is dealuminized mordenite.

9. The process of claim 3 wherein said catalyst is ZSM-5.

10. The process of claim 4 wherein said catalyst is ZSM-5.

11. The process of claim 1 wherein said reactor inlet temperature is from about 500° F to about 1100° F, said reactor pressure is from about 10 psig to about 70 psig, said catalyst/hydrocarbon compound weight ratio is from about 5 to about 40, said catalyst residence time is from about 0.5 second to about 20 seconds, and said hydrocarbon compound residence time is from about 0.5 second to about 20 seconds.

12. The process of claim 2 wherein said reactor inlet temperature is from about 500° F to about 1100° F, said reactor pressure is from about 10 psig to about 70 psig, said catalyst/hydrocarbon compound weight ratio is from about 5 to about 40, said catalyst residence time is from about 0.5 second to about 20 seconds, and said hydrocarbon compound residence time is from about 0.5 second to about 20 seconds.

13. The process of claim 1 wherein said alkylaromatic hydrocarbon compound having from 7 to 10 carbon atoms is selected from the group consisting of toluene, durene, xylene and homologs thereof and said transalkylating agent is an alkylaromatic hydrocarbon wherein alkyl is composed of from 1 to about 5 carbon atoms.

14. The process of claim 2 wherein said alkylaromatic hydrocarbon compound having from 7 to 10 carbon atoms is selected from the group consisting of toluene, durene, xylene and homologs thereof and said transalkylating agent is an alkylaromatic hydrocarbon wherein alkyl is composed of from 1 to about 5 carbon atoms.

15. The process of claim 3 wherein said alkylaromatic hydrocarbon compound having from 7 to 10 carbon atoms is selected from the group consisting of toluene, durene, xylene and homologs thereof and said transalkylating agent is an alkylaromatic hydrocarbon wherein alkyl is composed of from 1 to about 5 carbon atoms.

16. The process of claim 4 wherein said alkylaromatic hydrocarbon compound having from 7 to 10 carbon atoms is selected from the group consisting of toluene, durene, xylene and homologs thereof and said transalkylating agent is an alkylaromatic hydrocarbon wherein alkyl is composed of from 1 to about 5 carbon atoms.

17. The process of claim 13 wherein said transalkylating agent is selected from the group consisting of toluene, xylene, trimethylbenzene, triethylbenzene, dimethylethylbenzene, ethylbenzene, diethylbenzene and ethyltoluene.

18. The process of claim 17 wherein said alkylaromatic hydrocarbon compound is toluene.

19. The process of claim 17 wherein said alkylaromatic hydrocarbon compound is durene.

20. The process of claim 17 wherein said alkylaromatic hydrocarbon compound is xylene.

* * * * *